(12) United States Patent
Curtin et al.

(10) Patent No.: US 10,108,782 B2
(45) Date of Patent: Oct. 23, 2018

(54) SMART PNEUMATIC COUPLER (71) Applicant: Physio-Control, Inc., Redmond, WA (US)

(72) Inventors: Barry Curtin, Seattle, WA (US); Matthew Bielstein, Seattle, WA (US); Ian Barnes, Kirkland, WA (US); Ryan Apperson, Bothell, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 281 days.

(21) Appl. No.: 14/975,687

(22) Filed: Dec. 18, 2015

(65) Prior Publication Data
US 2016/0275258 A1 Sep. 22, 2016

Related U.S. Application Data

(60) Provisional application No. 62/094,031, filed on Dec. 18, 2014.

(51) Int. Cl.
| | |
|---|---|
| *G06F 19/00* | (2018.01) |
| *A61B 5/00* | (2006.01) |
| *A61B 5/08* | (2006.01) |
| *A61B 5/022* | (2006.01) |
| *A61B 5/0402* | (2006.01) |
| *A61B 5/145* | (2006.01) |
| *A61B 5/021* | (2006.01) |
| *G16H 40/63* | (2018.01) |
| *H04W 4/80* | (2018.01) |

(52) U.S. Cl.
CPC .......... *G06F 19/3406* (2013.01); *A61B 5/022* (2013.01); *A61B 5/02141* (2013.01); *A61B 5/0402* (2013.01); *A61B 5/082* (2013.01); *A61B 5/14542* (2013.01); *G16H 40/63* (2018.01); *H04W 4/80* (2018.02); *A61B 5/742* (2013.01); *A61B 5/7475* (2013.01); *A61B 2560/0266* (2013.01); *A61B 2560/0487* (2013.01); *A61B 2562/226* (2013.01)

(58) Field of Classification Search
CPC ..... G06F 19/3406; A61B 5/022; A61B 5/742; F16L 37/23
See application file for complete search history.

(56) References Cited

U.S. PATENT DOCUMENTS

| | | | | |
|---|---|---|---|---|
| 4,506,678 A | * | 3/1985 | Russell | A61B 5/0809 600/301 |
| 2005/0087235 A1 | * | 4/2005 | Skorpik | F16K 37/00 137/554 |
| 2006/0162713 A1 | * | 7/2006 | Carpenter | F41B 11/68 124/73 |
| 2009/0198605 A1 | * | 8/2009 | Ganzera | G06Q 20/327 705/35 |
| 2014/0213323 A1 | * | 7/2014 | Holenarsipur | H03K 17/955 455/566 |

* cited by examiner

*Primary Examiner* — Changhyun Yi
(74) *Attorney, Agent, or Firm* — Lane Powell PC (57) ABSTRACT

A pneumatic coupler having a pneumatic control device and a coupler detection module. The coupler detection module coupled to the pneumatic control device. The pneumatic coupler also having a signal bearing medium that is communicatively coupled to the coupler detection module and to a pneumatic device coupled to the pneumatic coupler. The signal bearing medium storing one or more of an identification of the pneumatic coupler and instructions for the pneumatic device.

16 Claims, 7 Drawing Sheets

SMART PNEUMATIC COUPLER

RELATED APPLICATION

This application claims benefit of priority to U.S. Provisional Patent Application Ser. No. 62/094,031 filed on Dec. 18, 2014, entitled CONNECTION DETECTION SYSTEM FOR PNEUMATIC COUPLER, which is incorporated herein by reference in its entirety.

BACKGROUND

Unless otherwise indicated herein, the approaches described in this section are not prior art to the claims in this application and are not admitted to be prior art by inclusion in this section.

As integration of functionalities in devices increases, more and more devices are being capable of a wide variety of applications. For example, in the health related fields, a singe health monitoring device may be capable of determining a wide variety of information about a person (e.g., by monitoring and/or measuring health related activities of the person). In order for the health monitoring device to determine the information, the health monitoring device may be communicatively coupled to various peripheral components. For example, a health monitoring device may include the capabilities of monitoring a person's oxygen saturation level. In order to determine the person's oxygen saturation level, a component such as a sensor may be coupled to the health monitoring device. Because the health monitoring device may be capable of other applications, the health monitoring device may detect the coupling of the sensor and automatically configure itself to provide the necessary functionality/interface for monitoring a person's oxygen saturation level. In other words, the health monitoring device may include plug and play functionality, where the health monitoring device may recognize the coupled component (e.g., the sensor) to be a component used for determining oxygen saturation level.

In another example, the health monitoring device may include electrocardiography (ECG) capabilities. As alluded to previously, in order to use the health monitoring device as an ECG device, a user may only need to couple (plug) a set of ECG electrodes with the health monitoring device. The health monitoring device may recognize the coupled electrodes as components used for determining a person's ECG, and accordingly, the health monitoring device may automatically configure itself to provide the functionalities of an ECG device (play) including necessary interfaces, displays, buttons, switches, etc.

As may be appreciated, the above described plug and play attributes of modern health monitoring devices may be more common in components that may have an electrical connection (e.g., sensor and electrodes). However, Information about a person's health may be discerned from a wide variety of health related activities of the person. One example of health related activity of the person may include activity related to a person's circulatory system.

Activity related to a person's circulatory system may include information regarding the person's blood pressure. Commonly, a person's blood pressure may be measured with a pneumatic related component such as, but not limited to, a blood pressure cuff.

In order to facilitate monitoring of a wide variety of health related activities of a person, sophisticated and intelligent health monitoring devices may be capable of monitoring a number of different health related activities of a person without too much user configuration (i.e., automatically plug and play).

SUMMARY

The present disclosure describes example methods, apparatus, and systems related to a smart pneumatic coupler apparatus. Example apparatus may include a pneumatic control device. The example apparatus may also include a coupler detection module coupled to the pneumatic control device. The example apparatus may also be a signal bearing medium. The signal bearing medium may be communicatively coupled to the coupler detection module. The signal bearing medium may be configured to be communicatively coupled to a pneumatic device, the pneumatic device being pneumatically coupled to the pneumatic coupler.

The present disclosure describes example methods, where an example method may include a method of operating a smart coupler apparatus. The example method may include at a coupler detection module, detecting a pneumatic coupling via a pneumatic control device. The example methods may further include generating an electrical signal upon detection of the pneumatic coupling, and transmitting the generated electrical signal to a pneumatically coupled device.

The present disclosure describes example machine readable non-transitory medium having stored instructions. The example machine readable non-transitory medium may include instructions that, when executed by one or more processors, operatively enable a coupler detection module to detect a pneumatic coupling via a pneumatic control device, generate an electrical signal upon detection of the pneumatic coupling, and transmit the generated electrical signal to a pneumatically coupled device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to a smart pneumatic coupler.

As devices become more integrated, a single device may have several functionalities. For example, in the healthcare related field, a single healthcare related device such as a health monitoring device may have a wide range of functionalities such as, but not limited to, measuring/monitoring a person's oxygen saturation level, a person's heart activity, a person's brain activity, and so forth. In order to use these functionalities, the health monitoring device may need to be configured for each functionality. For example, if the health monitoring device is to be used for measuring/monitoring a person's oxygen saturation level, the health monitoring device may need to be configured to receive, analyze, and provide information related to the oxygen saturation level. If subsequently, the health monitoring device is to be used for measuring a person's ECG, again, the health monitoring device may need to be configured to receive, analyze, and provide information related to the ECG functionality.

As part of the configuration, an interface (i.e., graphical, buttons, and/or physical switches) of the health monitoring device may need to be configured as well. For the previous example, as the health monitoring device is switched from the functionality of oxygen saturation level measuring/monitoring to the functionality of ECG measuring/monitoring, one may need to only switch out the components coupled to the health monitoring device to facilitate configuration of the interface of the health monitoring device. Once the sensor for measuring/monitoring the person's oxygen saturation level is decoupled from the health monitoring device and the electrodes for measuring/monitoring the person's ECG is coupled to the health monitoring device, the health monitoring device may automatically detect and recognize the type of functionality related to the coupled component (e.g., the electrodes), and accordingly, the health monitoring device may automatically configure the interface (i.e., graphical, buttons, and/or physical switches) of the health monitoring device to facilitate the new functionality (i.e., the ECG). As previously alluded to, the health monitoring device may have plug and play functionality.

However, in healthcare related situations, there may be several indicators of a person's health. For example, one indication of a person's health may include measuring a person's circulatory system such as, but not limited to, a person's blood pressure. Another example may include measuring a person's respiration such as, but not limited to, the concentration of various gases expelled by the person. Accordingly, it may be of no surprise that one of the acronyms a person may be taught when being taught first aid may be "CAB", which may stand for Compression, Airway, and Breathing (CAB).

In relation to circulation, a health monitoring device may facilitate determining perfusion of blood in a person's body (i.e., how well the blood is being delivered to the various parts of the body) and may have blood pressure measuring/monitoring functionality. In some cases, the health monitoring device having the blood pressure measuring/monitoring functionality may facilitate the diagnosis of potential circulatory issues such as, but not limited to, heart related issues, vital organ related issues, hypertension or hypotension (blood pressure too high or too low), etc. Accordingly, the health monitoring device may facilitate diagnosis of a wide range of health related issues.

In relation to breathing, a health monitoring device may have the functionality of measuring breathing and monitoring to facilitate determination of how well the person is being ventilated (i.e., is the person breathing well and exchanging gases appropriately). One example of a health monitoring device having the functionality of measuring breathing and monitoring may be having capnography functionality. The health monitoring device may be capable of monitoring the concentration of $CO_2$ at the end of each exhaled breath by the person. The concentration of $CO_2$ at the end of each exhaled breath may be known as end-tidal carbon dioxide ($ETCO_2$). The health monitoring device may provide information related to the cardiac output, pulmonary blood flow (i.e., perfusion) as the $CO_2$ and/or fractional $CO_2$ may be transported by the circulatory system to the right side of the heart and then pumped into the lungs by the right ventricle, alveolar ventilation at the lungs, respiratory issues, metabolism, etc. Accordingly, the health monitoring device having capnography functionality may facilitate diagnosis of a wide range of health related issues.

Blood pressure measuring/monitoring functionality and capnography functionality may both be considered to be pneumatic related functionalities (i.e., related to air/gas management) and may include the use of a pneumatic connector. For example, the blood pressure functionality may commonly involve management of inflation and deflation of a blood pressure monitor cuff. The blood pressure monitor cuff may be pneumatically coupled to the blood pressure device via a pneumatic connector. On the other hand, the capnography functionality may commonly involve management of a steady flow of exhaled gases for analysis via a pneumatic connector as well. Accordingly, there may be health monitoring devices, which may integrate a wide range of health monitoring capabilities such as, but not limited to, blood pressure monitoring, oxygen delivery, capnography, and so forth. Because a health monitoring device may have a wide range of capabilities, it may be beneficial if the health monitoring device could be automatically configured to detect the monitoring situation without too much manual configuration as previously described.

In a non-limiting example, if the health monitoring device detects that a pneumatic connector (e.g., a blood pressure cuff) was coupled, the health monitoring device may automatically configure itself to monitor a person's blood pressure without the person necessarily configuring the device. In another non-limiting example, the pneumatic connector may be configured to, once coupled to a health monitoring device, indicate to the health monitoring device its functionality, and the health monitoring device may configure itself accordingly.

Before moving on to the description of the figures, even though the above may have been mostly described with respect to pneumatic functionality it should be appreciated that it is contemplated within the present disclosure that the claimed subject matter may be applicable to a wide variety of health monitoring devices having a wide variety of functionalities such as, but not limited to, capnography functionality, continuous positive airway pressure (CPAP) functionality, gas delivery functionality (e.g., oxygen delivery), and so forth. Accordingly, the claimed subject matter is not limited in scope to the particular example implementations described herein.

In a non-limiting example, an integrated apparatus may include a blood pressure functionality, a capnography functionality, and/or a CPAP functionality, or any combination thereof. Additionally, these devices may be integrated as part of emergency equipment such as, but not limited to, a defibrillator or defibrillator/monitor device. As will be described in detail, the claimed subject matter may include these configurations and may include much more.

Because the disclosure may encompass a wide variety of healthcare related devices, it is contemplated within the present disclosure that the claimed subject matter applicable to a wide variety of healthcare related devices. For example, any and/or all of the devices previously mentioned may be included as a component of an electrical healthcare device such as, but not limited to, an advanced life support (ALS) type device. For example, an ALS defibrillator type device. The ALS defibrillator type device may include an external defibrillator type device.

An example type of ALS device may include defibrillator devices intended to treat multiple people, which may be commonly found in medical emergency rooms and other medical centers commonly for use by healthcare professionals. The ALS type devices may have a wide range of functionalities including allowing healthcare professionals to monitor a person's heart rhythm and manually intervene if is determined that a shock is necessary. Accordingly, some ALS type devices may included functionalities such as, but not limited to, blood pressure monitoring, capnography, etc.

In another example, the ALS type devices may include a defibrillator device intended to treat a limited number of people such as, but not limited to, a single person. Single person type external defibrillators may include relatively small (i.e., portable) external defibrillator devices. An example of a single person type external defibrillator may be an automated external defibrillator (AED) type device. AED type devices may be found in various private and/or public places such as, but not limited to, offices, train stations, airports, stadiums, hospitals, homes, vehicles, vessels, planes, trains, automobile, etc. AED type devices may be commonly for use by a layperson and/or a person with basic life support training.

Even though the present disclosure may be described with respect to healthcare monitoring devices, it will be appreciated that the claimed subject matter may be applicable to wide range devices, which may utilize pneumatic coupling. Accordingly, the claimed subject matter is not limited in these respects.

Figure 1:
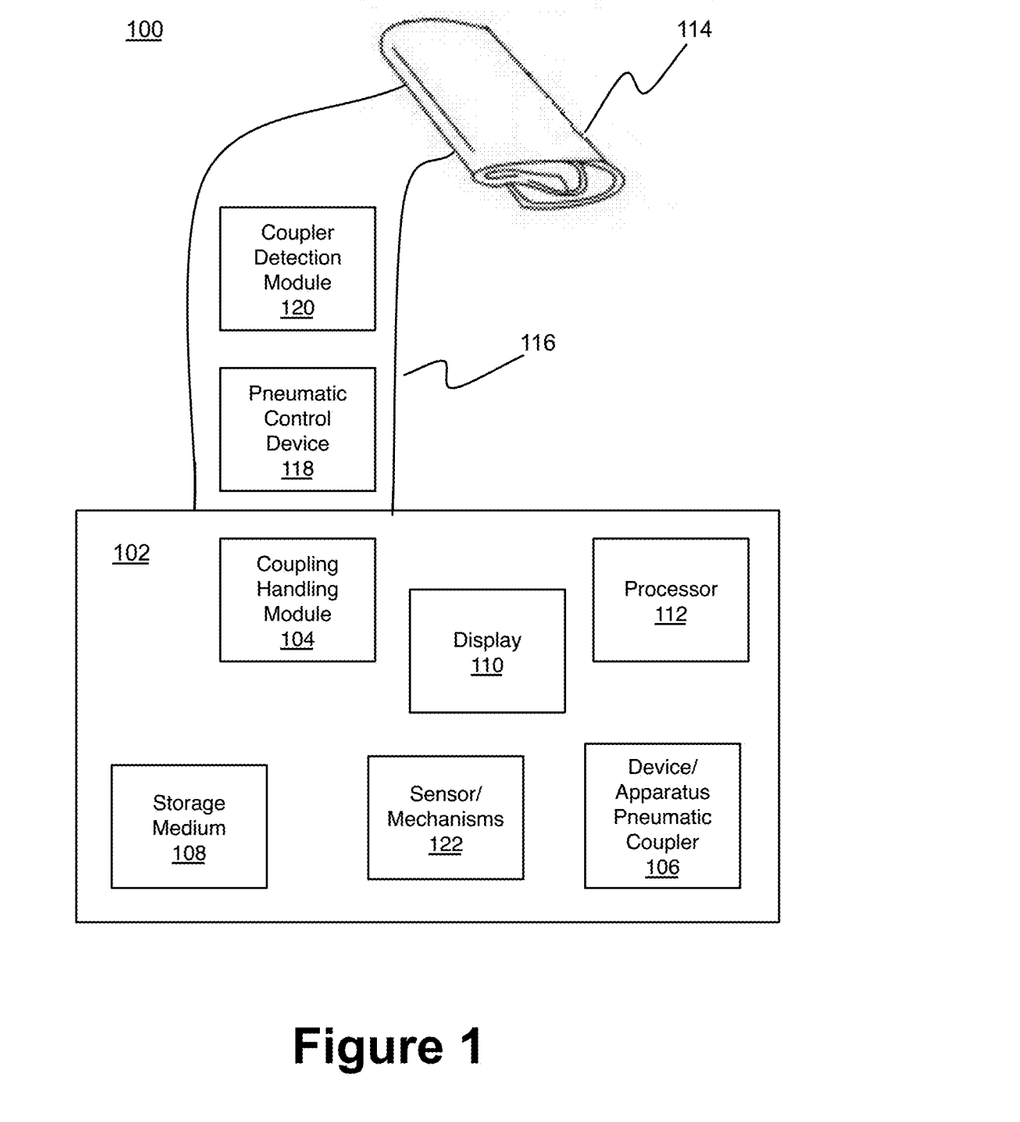
FIG. 1 illustrates block diagram of an example system in accordance with various embodiments.

Turning now to FIG. 1 (FIG. 1), where FIG. 1 illustrates block diagram of an example system in accordance with various embodiments. In FIG. 1, the system 100 may include a health monitoring device 102, which may include blood pressure monitoring functionality. The health monitoring device 102 may include a coupling handling module 104, a device/apparatus pneumatic coupler 106, a storage medium 108, a display 110, and a processor 112. In the example shown in FIG. 1, the system 100 may include a blood pressure cuff 114. The blood pressure cuff 114 may be coupled to a connector 116. The connector 116 may include a pneumatic control device 118 and a coupler detection module 120.

In a non-limiting scenario, the health monitoring device 102 and the connector 116 may be in an uncoupled position. When the connector 116 is coupled to the health monitoring device 102 via the device/apparatus pneumatic coupler 106, the coupler detection module 120 may detect the coupling via the pneumatic control device 118. For example, the pneumatic control device 118 may be a pneumatic valve type device such as, but not limited to, a poppet device. In one example, if the coupler detection module 120 detects that the pneumatic control device 118 is in a predetermined position (e.g., open or close/coupled or uncoupled), the coupler detection module 120 may generate an electrical signal and transmit the electrical signal to the coupling handling module 104 at the health monitoring device 102. The coupling handling module 104 may be communicatively coupled to the processor 112, the storage medium 108, and/or the display 110. The coupling handling module 104, the processor 112, and/or the storage medium may be configured to facilitate functionality of the health monitoring device 102 in accordance with the electrical signal received by the coupling handling module 104 from the coupler detection module 120 at the connector 116. For example, the display device 110 may be a display device configured to facilitate a user interface such as, but not limited to, a graphical user interface. Accordingly, in this example, the display device 110 may provide graphical functionality to facilitate blood pressure monitoring and/or measuring. In one embodiment, the blood pressure device is detected by the monitoring device 102 and becomes automatically readily perceivable to a user. Such health monitoring device 102 may utilize the presence of such information and react to adjust or facilitate additional controls, such as soft controls, to a user. In a further embodiment, a user may then elect whether s/he wishes to see parameters gathered from one accessory or another accessory or yet have all incoming through a user interface, whether it is a display 110, or visual or audio (not shown) or a combination thereof. In a further embodiment, a detection of an accessory, such as the blood pressure cuff, may be based on whether or not the accessory is connected to a patient and ready to collect or collecting data. Here, the presence of a blood pressure cuff would be detected when actual connection between a data gathering device, such as monitoring device 102 and patient is established. Such connection may be determined using, for example, a smart sensor 122.

Here it should be pointed out that even though the above non-limiting example scenario is described with respect to blood pressure functionality, it should be appreciated that it is contemplated that a wide range of scenarios may be applicable. Another non-limiting example may include a connector, which may be used for capnography purposes, coupled to a health monitoring device having capnography functionality. The coupler detection module 120 may, upon detection of connection of the pneumatic control device 118, generate an electrical signal and transmit the electrical signal to the health monitoring device. Upon receiving the electrical signal, the health monitoring device may automatically configure itself to provide capnography functionality, in accordance with various embodiments. For example, the health monitoring device may include the display 110, which may automatically configure itself to provide a graphical user interface to facilitate capnography functionality similar to the above described scenarios.

Another non-limiting example may include a connector being, which may be used for CPAP purposes, coupled to a health monitoring device having CPAP device functionality. The coupler detection module 120 may, upon detection of connection of the pneumatic control device 118, generate an electrical signal and transmit the electrical signal to the health monitoring device. Upon receiving the electrical signal, the health monitoring device may automatically configure itself to provide CPAP functionality, in accordance with various embodiments. For example, the health monitoring device may include the display 110, which may automatically configure itself to provide a graphical user interface to facilitate CPAP functionality similar to the above described scenarios.

It should be appreciated that as devices become more integrated, it is contemplated that the claimed subject matter may be applicable to a device, which may have multiple functionalities. For example, in the previously described examples, a single device may have blood pressure measuring functionality, capnography functionality, ECG functionality, oxygen saturation level functionality, brain activity measuring functionality, a CPAP functionality, and so forth, or any combination thereof. Accordingly, the claimed subject matter is not limited in these respects. For this example, a display may provide graphical functionality to facilitate utilization of each of these functionalities in a single device or utilization of one, or potentially more intelligent, couplers, whether pneumatic or otherwise, capable of determining the type of accessory being connected to it. Additionally, in order to facilitate interaction and facilitate utilization of each of these functionalities in a single device, a health monitoring device may configure buttons, switches, software, color, form factor, etc., and/or any combination thereof based on the information being conveyed from the accessory and/or coupler. Accordingly, the claimed subject matter is not limited in these respects.

It should be appreciated that it is contemplated within the scope of disclosure that the claimed subject matter may be applicable to a wide variety of devices/apparatus that may include a pneumatic, and or other types of coupling, or coupler combinations such as, but not limited to, pumps, vacuums, pressurized tank management, self-contained underwater breathing apparatus (scuba), welding apparatus, etc. Accordingly, the claimed subject matter is not limited in these respects.

Continuing with the non-limiting example of a blood pressure functionality, in FIG. 1, the connector 116 may facilitate inflation of the blood pressure cuff 114. The inflation of the blood pressure cuff 114 via the connector 116 may facilitate measurement of a blood pressure of a person (not shown). Accordingly, the health monitoring device 102 may be configured to inflate and deflate the blood pressure cuff 114 via the connector 116 and determine a systolic and a diastolic blood pressure of the person. That is determine if the blood pressure cuff is at or above a person's systolic pressure, and if it is determined that the blood pressure cuff is at or above the person's systolic pressure, deflate the blood pressure cuff, and determine a systolic pressure and a diastolic pressure based, at least in part, on the deflation of the blood pressure.

In another example, the health monitoring device 102 may be have non-invasive blood pressure (NIBP) measuring and monitoring type functionality. Accordingly, the health monitoring device 102 may include sensors and/or mechanisms (hereon out, sensors) 122 to facilitate oscillometric functionality for the health monitoring device 102. For example, the health monitoring device 102 may be configured to determine an amplitude of a person's pulse as the blood pressure cuff 114 is deflated from above a systolic pressure, determine a sudden increase in the amplitude, determine a diastolic pressure based, at least in part, on a transition of the amplitude from a maximum. Additionally, the health monitoring device 102 may include sensors 122 to facilitate auscultatoric functionality for the blood pressure device 200. For example, the sensors 122 of the health monitoring device 102 may include audio sensors (not shown) to help facilitate detection of flow of blood, which may be referred to as Korotkoff sounds. The Korotkoff sounds may help facilitate determination of systolic blood pressure and diastolic arterial pressure.

In one example, the coupler detection module 120 may comprise of a transducer type device, where the coupler detection module 120 may be configured to convert a change in pneumatic pressure to an electrical signal. In another example, the coupler detection module 120 may comprise of a proximity detection device, where the coupler detection module 120 may utilize an optical proximity detection device to optically detect a coupling with a device/apparatus. In another example, the coupler detection module 120 may comprise of a physical switch, where the physical switch may be activated when a connector is coupled to a device/apparatus.

In one example, a coupler detection module 120 may include a processor, a storage medium, and a radio device. That is, a coupler detection module 120 may have the functionality of a radio frequency identification (RFID) tag. The RFID tag functionality may include passive RFID tag, active RFID tag (e.g., a coupler detection module 120 may also include a power supply), and/or a semi-active RFID tag. Additionally, the RFID tag may be configured to utilize capacitive technology. In the example where the coupler detection module 120 may have RFID functionality, a device/apparatus pneumatic coupler 106 may include corresponding RFID functionality. For example, in the case of a passive RFID functionality, when a connector is proximate a device/apparatus, the coupler detection module 120 may detect an electric field from the device/apparatus and generate and transmit an electrical signal to the device/apparatus. In another example, in the case of an active RFID functionality, when a connector is at a predetermined distance from device/apparatus, the device/apparatus may receive an electrical signal from the coupler detection module 120.

In one example, where the coupler detection module 120 may include a storage medium, the coupler detection module 120 may be configured to store a person's blood pressure measurement to facilitate download of the person's history. For example, the coupler detection module 120 store a person's blood pressure history and/or the number of times the blood pressure cuff 114 and the connector 116 may have been coupled to different devices and/or the same device (i.e., NIBP device). The stored history may be downloaded at a later time. In another example, the blood pressure cuff 114 and the connector 116 may have a predetermined life cycle (i.e., may be used for a predetermined number of cycles for accuracy). Here again, the coupler detection module 120 may store the number of times the blood pressure cuff 114 and the connector 116 have been used. Additionally, the blood pressure cuff 114 and the connector 116 coupling may have a predetermined life cycle. Accordingly, the coupler detection module 120 may store the number of times the blood pressure cuff 114 and the connector 116 may have been coupled to various devices.

In yet another example, where the coupler detection module 120 may include a storage medium, the storage medium may store information related to facilitating functionality of the pneumatically coupled device. For example, the coupler detection module 120 may provide the coupling handling module 104 data corresponding to generating a graphical user interface at the display 110. In the non-limiting example of the BP device 102, the graphical user interface to facilitate functionality may be received by the BP device 102 from the coupler detection module 120 (i.e., information stored at a storage device included in the coupler detection module 120).

In FIG. 1, it is contemplated within the scope of the claimed subject matter that the blood pressure cuff 114 may be a self contained blood pressure cuff. For example, the various example components described with respect to a health monitoring device 102 may be included in the blood pressure cuff 114. In this non-limiting example, the connector 116, pneumatic control device 118, and/or the device/apparatus pneumatic coupler 106 may not be present. Continuing with the self contained health monitoring device example, the coupler detection module 120 may be configured to detect when the blood pressure cuff 114 is placed on a person's arm. Additionally, in addition to facilitating oscillometric functionality for the health monitoring device 102, the sensors 122 may be configured to detect human capacitance (e.g., capacitive coupling). Accordingly, when the blood pressure cuff 114 is placed on a person, the coupler detection module 120 may communicatively transmit its functionality to a communicatively coupled device. In one example, the functionality may be communicatively transmitted wirelessly.

In another example, the functionality may be communicatively transmitted using a physical connection. The communication may be bi-directional, and accordingly, in the non-limiting example of wirelessly communicatively coupled device, health monitoring device may receive communication from the wirelessly communicatively coupled device.

It should be appreciated that the described wireless functionality may include a wireless communication component such as, but not limited to, a radio type device configured to transmit and/or receive wireless signals. The wireless signals may include a wide variety of wireless signals such as, Bluetooth, WiFi, near field communication (NFC), cellular, etc., and accordingly, the claimed subject matter is not limited in these respects.

In another example, in addition to facilitating oscillometric functionality for the health monitoring device 102, the sensors 122 may be configured to a heart rate of the person (e.g., infrared sensors).

It is contemplated within the scope of the claimed subject matter that a health monitoring device may include a wide variety of health monitoring devices including devices having health monitoring functionality but not necessarily a health monitoring device such as, but not limited to, a handheld device, a smart phone, a tablet type device, portable computer, etc. For example, a health monitoring device may be smart phone having a health monitoring related application. In this non-limiting example, the self contained blood pressure cuff may provide the information to generate a graphical user interface to facilitate functionality of a blood pressure monitor to the smart phone.

Accordingly, a health monitoring device may detect a coupling and/or configure itself to facilitate utilization of the coupling and its corresponding functionality.

Figure 2:
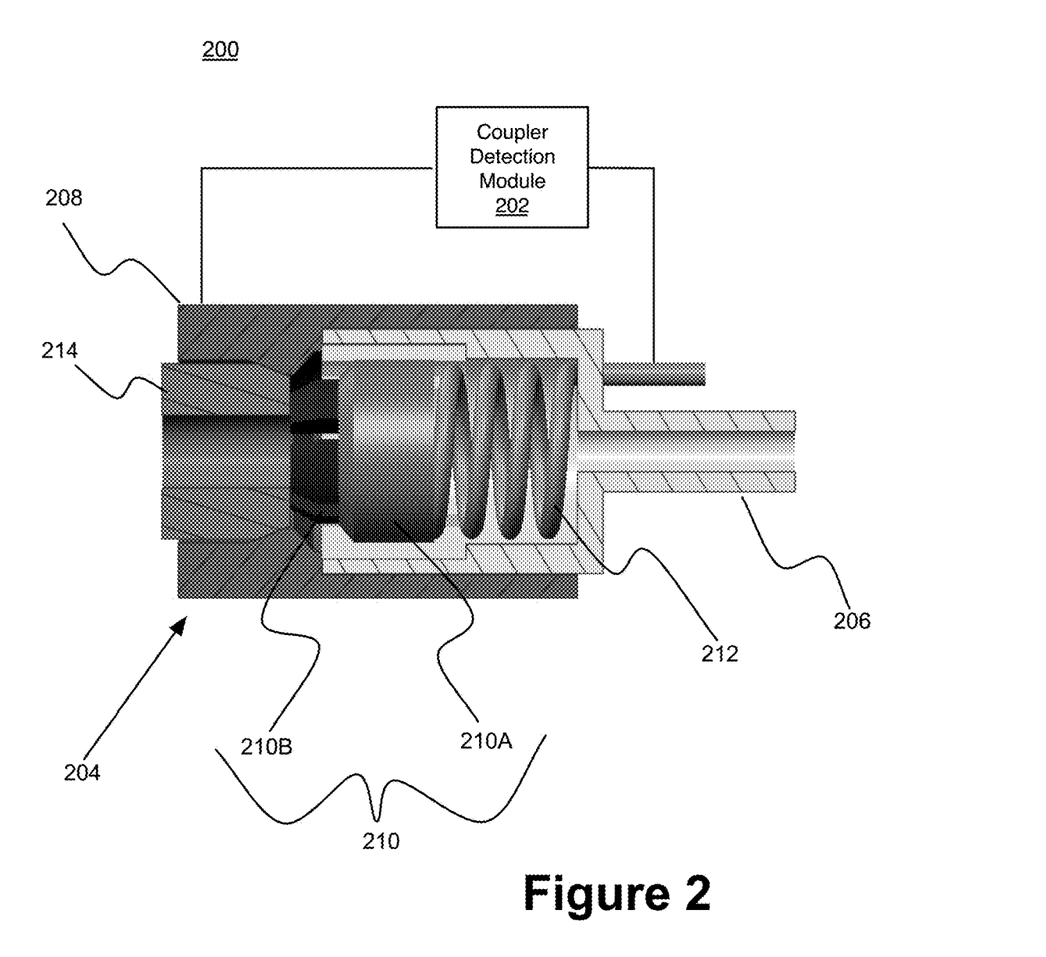
FIG. 2 illustrates a pneumatic coupler in accordance with various embodiments.

FIG. 2 illustrates a pneumatic coupler in accordance with various embodiments. In FIG. 2, a pneumatic coupler 200 may include a coupler detection module 202 and a pneumatic control device 204. It should be pointed out that the pneumatic coupler 200 may be described with labels of components similar to the components described with respect to FIG. 1. However, it should be appreciated that the components may be different types of components and may not necessarily be the same or similar components. In the example shown in FIG. 2, the pneumatic control device 204 may include a coupler end cap 206, a coupler body 208, a poppet valve assembly 210 having a poppet 210A and an isolator 210B, and a spring 212. Additionally shown, a device/apparatus pneumatic coupler 214, which may be mating coupler on a device/apparatus as previously described.

In FIG. 2, pneumatic control device 204 may be electrically coupled between the poppet assembly 210 and the coupler body 208. In one example, in a non-connected state, the poppet assembly 210 may be in contact with the coupler body 208 and may correspond to a closed circuit. Alternatively, if the poppet assembly 210 is not in contact with the coupler body 208, the configuration may be considered to be an open circuit.

In one example, the coupler end cap 206 may comprise of a non-conductive material while the coupler body 208 may comprise of a conductive material. Additionally, the spring 212 may comprise of a conductive material, and the spring 212 may make electrical contact with the poppet assembly 210 and may extend through the coupler end cap 206 facilitating an electrical connection between the pneumatic control device 204 and the poppet assembly 210.

In one example, in an electrically non-connected state, the poppet 201A may comprise of a conductive material and may be pushed against the inside of the coupler body 208, which also may comprise of a conductive material, by way of the spring 212, which may also comprise of a conductive material. In the electrically non-connected state, the pneumatic control device 204 may be completed and the measure may be closed.

In one example, in an electrically connected state, the device/apparatus pneumatic coupler 214 may push on the isolator 2106. The isolator 2106 may comprise of a non-conductive material. Accordingly, the poppet 210A may be pushed away from the coupler body 208, and the circuit may be broken and the measure may be open.

In these examples, the isolator 2106 may comprise of a non-conductive material and may help facilitate prevention of the device/apparatus pneumatic coupler 214 making an electrical connection between the poppet 210A and the coupler body 208, which may cause a closed circuit resulting in the coupling not being detected.

In another example, the outside surface of the coupler end cap 206, at an interface between the coupler end cap 206 and the coupler body 208 may be coated with a conductive material. The coupler end cap 206 may include an electrical terminal (not shown) to facilitate an electrical connection between the coupler end cap 206 and the coupler detection module 202. In this example, the coupler end cap 206 may comprise of a conductive material. A local insulating material (not shown) may be disposed between the coupler end cap 206 and the coupler body 208. In order to facilitate an electrical connection, the spring 212 may not need to pass through the coupler end cap 206.

In another example, a conductive washer or plate having an electrical terminal (not shown) may be included in the coupler end cap 206. The conductive washer or plate may facilitate an electrical connection between the coupler detection module 202 and the spring 212. In another example, a metal molded process may be employed.

In yet another example, a local conductive pad (not shown) may be disposed substantially behind the poppet 210A. The coupler detection module 202 may be communicatively coupled between the conductive pad and the spring 212. In a connected state, the poppet 210A may close an electrical connection between the conductive pad and the spring 212. The isolator 210B may no longer needed and electrical isolation of the coupler body 208 may be facilitated for various applications.

Figure 3:
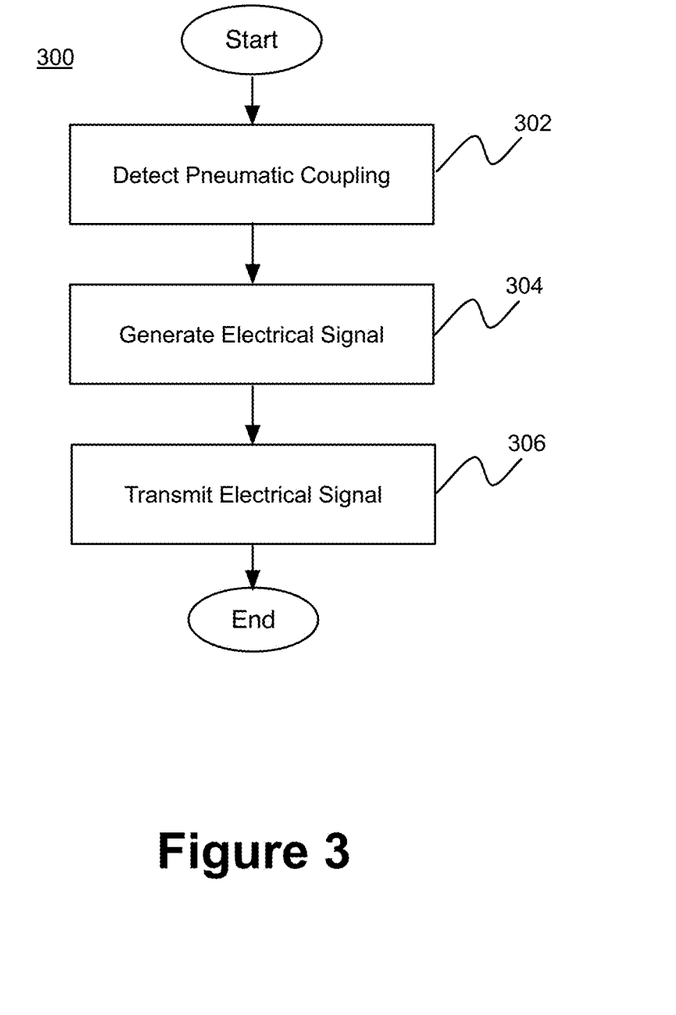
FIG. 3 illustrates an operational flow for a smart pneumatic coupler, arranged in accordance with at least some embodiments described herein.

FIG. 3 illustrates an operational flow for a smart pneumatic coupler, arranged in accordance with at least some embodiments described herein. In some portions of the description, illustrative implementations of the method are described with reference to the elements of the components described with respect to FIGS. 1 and 2. However, the described embodiments are not limited to these depictions. More specifically, some elements depicted in FIGS. 1 and 2 may be omitted from some implementations of the methods details herein. Furthermore, other elements not depicted in FIGS. 1 and 2 may be used to implement example methods detailed herein.

Additionally, FIG. 3 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 300 may be employed as part of a smart pneumatic coupler apparatus. As previously described, the smart pneumatic coupler apparatus may include a pneumatic control device, a coupler detection module, and a signal bearing medium.

Beginning at block 302 ("Detect Pneumatic Coupling"), the coupler detection module 120 may detect a pneumatic coupling via a pneumatic control device 118 (both shown in FIG. 1) The pneumatic control device 118 may be of a wide range of pneumatic control devices such as, but not limited to, a pneumatic valve, a poppet, a diaphragm, etc.

Continuing from block 302 to 304 ("Generate Electrical Signal"), upon detection of the coupling, such as pneumatic coupling (302), the coupler detection module 120 may generate an electrical signal and proceed to transmit the electrical signal to a corresponding device/apparatus, at block 306 ("Transmit Electrical Signal").

In general, the operational flow described with respect to FIG. 3 and elsewhere herein may be implemented as a computer program product, executable on any suitable computing system, or the like. For example, a computer program product for facilitating utilization of a smart pneumatic coupler apparatus. Example computer program products may be described with respect to FIG. 4 (FIG. 4) and elsewhere herein.

Figure 4:
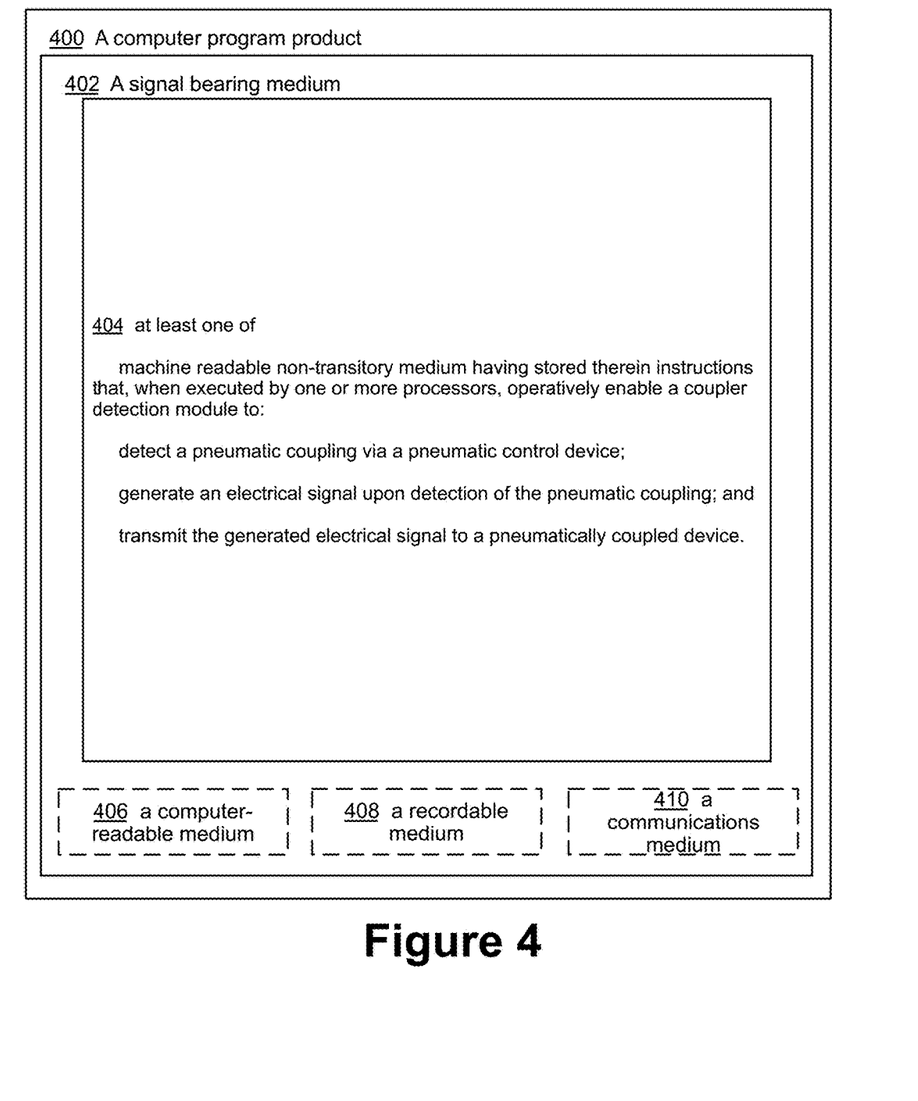
FIG. 4 illustrates an example computer program product, arranged in accordance with at least some embodiments described herein.

FIG. 4 illustrates an example computer program product 400, arranged in accordance with at least some embodiments described herein. Computer program product 400 may include machine readable non-transitory medium having stored therein instructions that, when executed, cause the machine to utilize smart pneumatic coupler apparatus, according to the processes and methods discussed herein. Computer program product 400 may include a signal bearing medium 402. Signal bearing medium 402 may include one or more machine-readable instructions 404, which, when executed by one or more processors, may operatively enable a computing device to provide the functionality described herein. In various examples, the devices discussed herein may use some or all of the machine-readable instructions.

In some examples, the machine readable instructions 404 may include instructions that, when executed, cause the machine to detect a pneumatic coupling via a pneumatic control device. In some examples, the machine readable instructions 404 may include instructions that, when executed, cause the machine to upon detection of the pneumatic coupling, generate an electrical signal. In some examples, the machine readable instructions 404 may include instructions that, when executed, cause the machine to transmit the generated electrical signal to a pneumatically coupled device.

In some implementations, signal bearing medium 402 may encompass a computer-readable medium 406, such as, but not limited to, a hard disk drive, a Compact Disc (CD), a Digital Versatile Disk (DVD), a digital tape, memory, etc. In some implementations, the signal bearing medium 402 may encompass a recordable medium such as, but not limited to, memory, read/write (R/W) CDs, R/W DVDs, etc. In some implementations, the signal bearing medium 602 may encompass a communications medium such as, but not limited to, a digital and/or an analog communication medium (e.g., a fiber optic cable, a waveguide, a wired communication link, a wireless communication link, etc.). In some examples, the signal bearing medium 402 may encompass a machine readable non-transitory medium.

In general, the methods described with respect to FIG. 4 and elsewhere herein may be implemented in any suitable computing system. Example systems may be described with respect to FIG. 5 and elsewhere herein. In general, the system may be configured to facilitate utilization of a smart pneumatic coupler apparatus.

Figure 5:
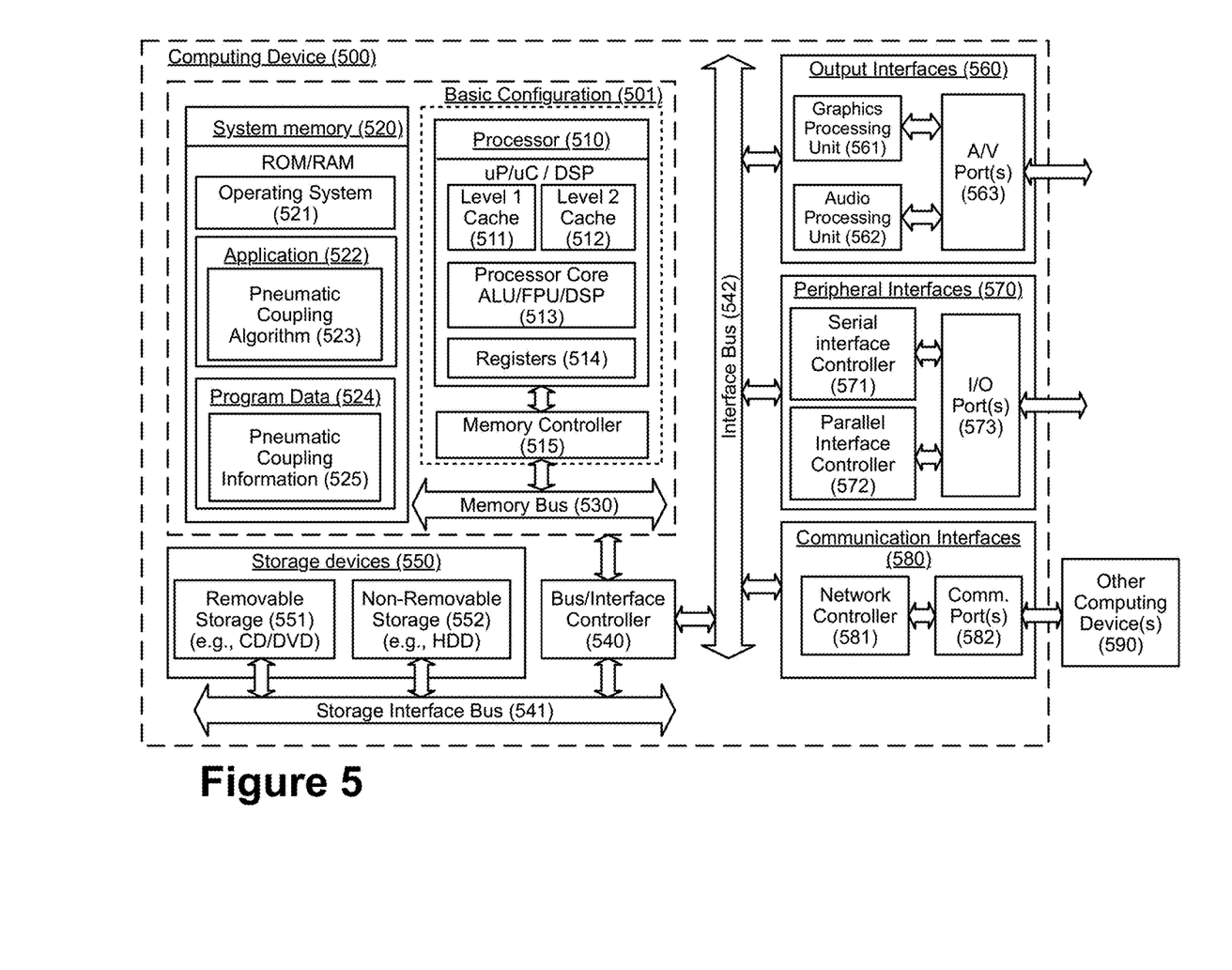
FIG. 5 is a block diagram illustrating an example computing device 500, such as might be embodied by a person skilled in the art, which is arranged in accordance with at least some embodiments of the present disclosure.

FIG. 5 (FIG. 5) is a block diagram illustrating an example computing device 500, such as might be embodied by a person skilled in the art, which is arranged in accordance with at least some embodiments of the present disclosure. In one example configuration 501, computing device 500 may include one or more processors 510 and system memory 520. A memory bus 530 may be used for communicating between the processor 510 and the system memory 520.

Depending on the desired configuration, processor 510 may be of any type including but not limited to a microprocessor (μP), a microcontroller (μC), a digital signal processor (DSP), or any combination thereof. Processor 510 may include one or more levels of caching, such as a level one cache 511 and a level two cache 512, a processor core 513, and registers 514. The processor core 513 may include an arithmetic logic unit (ALU), a floating point unit (FPU), a digital signal processing core (DSP Core), or any combination thereof. A memory controller 515 may also be used with the processor 510, or in some implementations the memory controller 515 may be an internal part of the processor 510.

Depending on the desired configuration, the system memory 520 may be of any type including but not limited to volatile memory (such as RAM), non-volatile memory (such as ROM, flash memory, etc.) or any combination thereof. System memory 520 may include an operating system 521, one or more applications 522, and program data 524. Application 522 may include pneumatic coupling algorithm 523 that is arranged to perform the functions as described herein including the functional blocks and/or actions described. Program Data 524 may include, among many information described, pneumatic coupling detection information 525 for use with pneumatic coupling control algorithm 523. In some example embodiments, application 522 may be arranged to operate with program data 524 on an operating system 521 such that implementations of a multifunctional healthcare monitoring apparatus may be provided as described herein. For example, apparatus described in the present disclosure may comprise all or a portion of computing device 500 and be capable of performing all or a portion of application 522 such that implementations of multifunctional healthcare monitoring apparatus may be provided as described herein. This described basic configuration is illustrated in FIG. 5 by those components within dashed line 501.

Computing device 500 may have additional features or functionality, and additional interfaces to facilitate communications between the basic configuration 501 and any required devices and interfaces. For example, a bus/interface controller 540 may be used to facilitate communications between the basic configuration 501 and one or more data storage devices 550 via a storage interface bus 541. The data storage devices 550 may be removable storage devices 551, non-removable storage devices 552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 520, removable storage 551 and non-removable storage 552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of device 500.

Computing device 500 may also include an interface bus 542 for facilitating communication from various interface devices (e.g., output interfaces, peripheral interfaces, and communication interfaces) to the basic configuration 501 via the bus/interface controller 540. Example output interfaces 560 may include a graphics processing unit 561 and an audio processing unit 562, which may be configured to communicate to various external devices such as a display or speakers via one or more A/V ports 563. Example peripheral interfaces 560 may include a serial interface controller 571 or a parallel interface controller 572, which may be configured to communicate with external devices such as input devices (e.g., keyboard, mouse, pen, voice input device, touch input device, etc.) or other peripheral devices (e.g., printer, scanner, etc.) via one or more I/O ports 573. An example communication interface 580 includes a network controller 581, which may be arranged to facilitate communications with one or more other computing devices 590 over a network communication via one or more communication ports 582. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 500 may also be implemented as a personal computer including both laptop computer and non-laptop computer configurations. In addition, computing device 500 may be implemented as part of a wireless base station or other wireless system or device.

Figure 6:
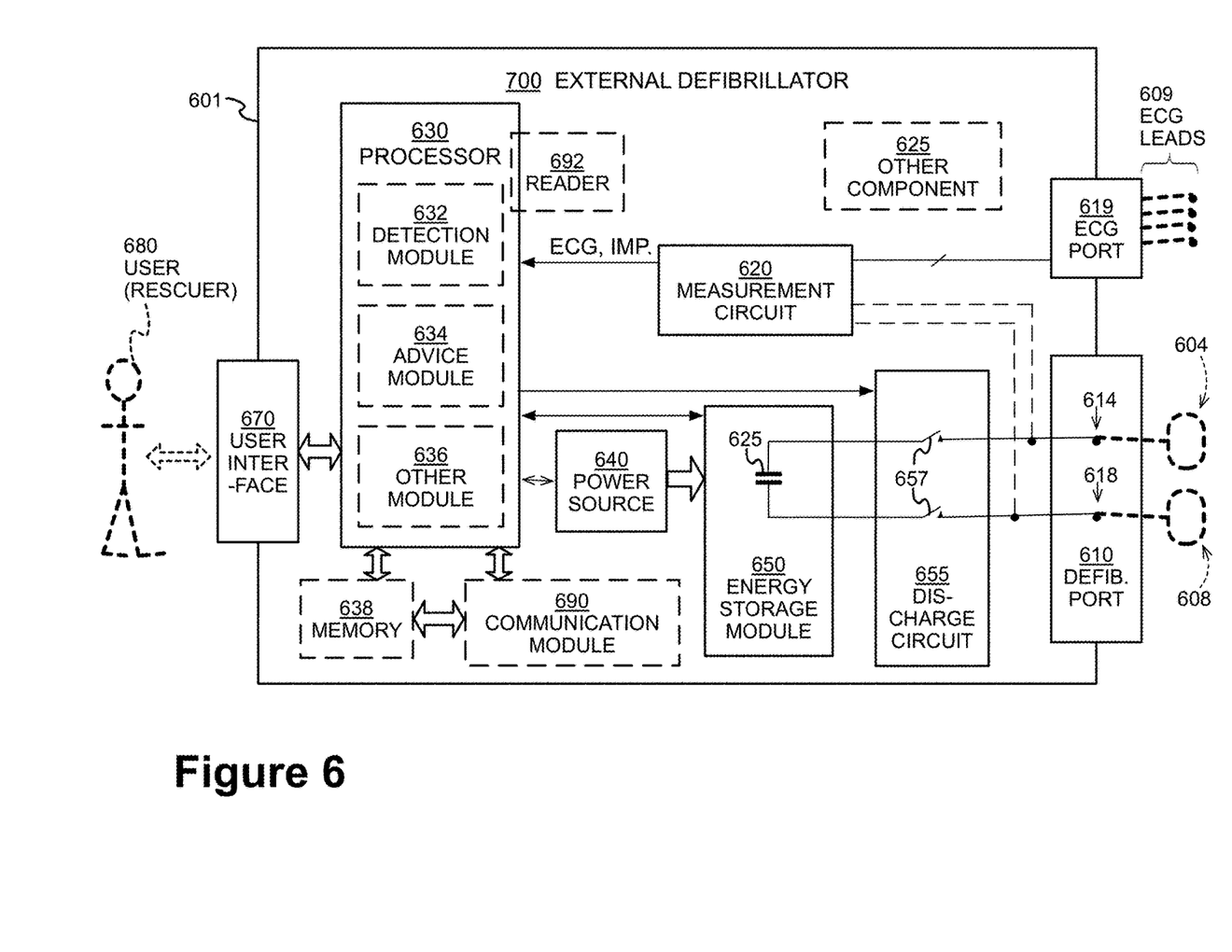
FIG. 6 is a block diagram illustrating components of health monitoring device which may be used with various embodiment disclosed herein.

FIG. 6 (FIG. 6) is a block diagram illustrating components of health monitoring device which may be used with various embodiment disclosed herein. In the example shown in FIG. 6, a health monitoring device may be a defibrillator device 600. These components may be, for example, pneumatically coupled with the various components and embodiments described with respect to FIGS. 1-5. The components of FIG. 6. may be provided in a housing 601, which may be known as casing 601.

The defibrillator device 600 may be intended for use by a user 680 (e.g., a rescuer). The defibrillator device 600 may typically include a defibrillation port 610, such as a socket in housing 601. The defibrillation port 610 may include nodes 614 and 618. One or more electrodes 604 and 608 may be plugged in to the defibrillation port 610, so as to make electrical contact with nodes 614 and 618, respectively. It may also be possible that the electrodes 604 and 608 may be connected continuously to the defibrillation port 610, etc. Either way, the defibrillation port 610 may be used for guiding via the electrodes 604 and 608 to a person an electrical charge that may have been stored in the defibrillator device 600, as described herein.

If the defibrillator device 600 comprise of a defibrillator-monitor and the defibrillator device 600 may also have an ECG port 619 in the housing 601, for receiving ECG leads 609. The ECG leads 609 may facilitate sensing of an ECG signal (e.g., a 12-lead signal or from a different number of lead signals). Moreover, a defibrillator-monitor could have additional ports (not shown), and the other component 625 may be configured to filter the ECG signal (e.g., application of at least one filter to the signal to help facilitate removal of artifacts such as, but not limited to, chest compression due to chest compressions being delivered to the person).

The defibrillator 600 also may include a measurement circuit 620. The measurement circuit 620 may receive physiological signals from the ECG port 619, and also from other ports, if provided. The circuit 620 may render detected physiological signals and their corresponding information. The information may be in the form of data, or other signals, etc.

If the defibrillator 600 is configures as an AED type device, ECG port 619 may not be present. The measurement circuit 620 may obtain physiological signals through the nodes 614 and 618 instead, when the electrodes 604 and 608 are attached to the person, as previously described. In these cases, a person's ECG signal may be detected as a voltage difference between the electrodes 604 and 608. Additionally, the impedance between the electrodes 604 and 608 may be detected, among other things, whether the electrodes 604 and 608 have been inadvertently disconnected from the person.

The defibrillator 600 may also include a processor 630. The processor 630 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 630 may include a number of modules. One example module may be a detection module 632, which may detect outputs from the measurement circuit 620. The detection module 632 may include a VF detector. Accordingly, the person's detected ECG may be utilized to help determine whether the person is experiencing VF.

In another example module may be an advice module 634, which may provide advice based, at least in part, on outputs of detection module 632. The advice module 634 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 600 may further issue prompts for administrating CPR, and so forth.

The processor 630 may include additional modules, such as module 636 for various other functions. Additionally, if other component 625 is provided, it may be operated in part by processor 630, etc.

In an example, the defibrillator device 600 may include a memory 638, which may work together with the processor 630. The memory 638 may be implemented in a wide variety of manners. For example, the memory 638 may be implemented such as, but not limited to, nonvolatile memories (NVM), read-only memories (ROM), random access memories (RAM), and so forth or any combination thereof. The memory 638 may can include programs for the processor 630, and so on. The programs may include operational programs execution by the processor 630 and may also include protocols and methodologies that decisions may be made by advice module 634. Additionally, the memory 638 may store various prompts for the user 680, etc. Moreover, the memory 638 may store a wide variety of information (i.e., data) such as, but not limited to information regarding the person.

The defibrillator 600 may also include a power source 640. In order to facilitate portability of defibrillator device 600, the power source 640 may include a battery type device. A battery type device may be implemented as a battery pack, which may be rechargeable or not be rechargeable. At times, a combination of rechargeable and non-rechargeable battery packs may be utilized. Examples of power source 640 may include AC power override, where AC power may be available, and so on. In some examples, the processor 630 may control the power source 640.

Additionally, the defibrillator device 600 may include an energy storage module 650. The energy storage module 650 may be configured to store some electrical energy (e.g., when preparing for sudden discharge to administer a shock). The energy storage module 650 may be charged from the power source 640 to an appropriate level of energy, as may be controlled by the processor 630. In some implementations, the energy storage module 650 may include one or more capacitors 652, and the like.

The defibrillator 600 may include a discharge circuit 655. The discharge circuit 655 may be controlled to facilitate discharging of the energy stored in energy storage module 650 to the nodes 614 and 618, and also to electrodes 604 and 608. The discharge circuit 655 may include one or more switches 657. The one or more switches 657 may be configured in a number of manners such as, but not limited to, an H-bridge, and so forth.

The defibrillator device 600 may further include a user interface 670 for the user 680. The user interface 670 may be implemented in a variety of manners. For example, the user interface 670 may include a display screen capable of displaying what is detected and measured, provide visual feedback to the user 680 for their resuscitation attempts, and so forth. The user interface 670 may also include an audio output such as, but not limited to, a speaker to issue audio prompts, etc. The user interface 670 may additionally include various control devices such as, but not limited to, pushbuttons, keyboards, switches, track pads, and so forth. Additionally, the discharge circuit 655 may be controlled by the processor 630 or directly by the user 680 via the user interface 670, and so forth.

Additionally, the defibrillator device 600 may include other components. For example, a communication module 690 may be provided for communicating with other machines as previously described. Such communication may be performed wirelessly, or via wire, or by infrared communication, and so forth. Accordingly, information may be communicated, such as person data, incident information, therapy attempted, CPR performance, ECG information, and so forth.

A feature of a defibrillator device may be CPR related prompting. CPR prompts may be issued to the user 680 visually or by audio facilitating assistance in the administration of CPR by the user 680. Examples may be found in U.S. Pat. Nos. 6,334,070 and 6,356,785.

Figure 7A:
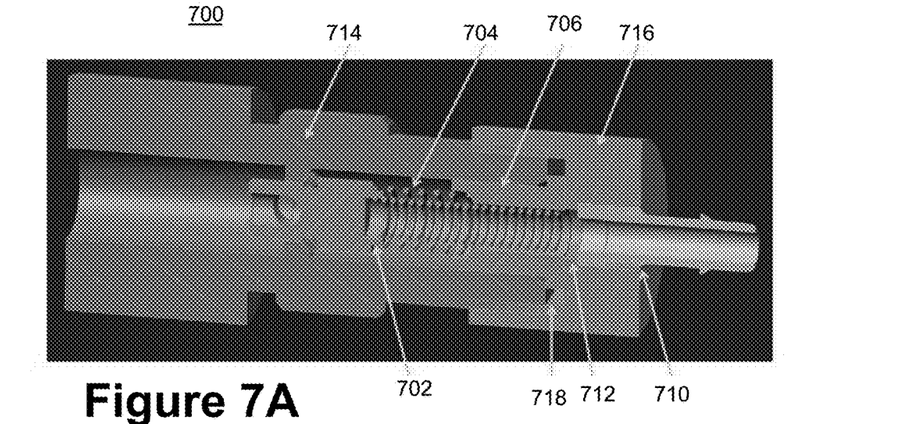
FIGS. 7A-7C a pneumatic coupler in accordance with various embodiments.

FIG. 7A illustrates a pneumatic coupler in accordance with various embodiments. In FIG. 7A, a pneumatic coupler 700 may include various components. However, before describing the various components of FIG. 7A, it should be pointed out that the pneumatic coupler 700 may be described with labels of components similar to the components described with respect to FIGS. 1 and 2. However, it should be appreciated that the components may be different types of components and may not necessarily be the same or similar components. In FIG. 7A, the pneumatic coupler 700 may include a poppet 702, a poppet spring 704, a brass/metal insert 706, and a second internal spring 708. In one example, the poppet 702, the poppet spring 704, the brass/metal insert 706, and the second internal spring 708 may be electrically coupled to an electrical network. This electrical network may be electrically coupled to one side of a coupler detection module, which in this example may be a sense circuit. A second side of the sense circuit may be electrically coupled to an air exit barb 710. The air exit barb 710 may be isolated from a main body of the pneumatic coupler 700 with an isolation component 712. When a mating pneumatic coupler may be coupled, the poppet 702 may be displaced, which may result in the internal spring 708 making contact with a back of the barb 710, and accordingly, the sense circuit may be completed.

In one example, the barb 710 may be co-molded to the electrical isolation component 712. In another example, the barb 710 may be mechanically attached to the electrical isolation component 712.

Using the second internal spring 708 may facilitate reduced impedance to the air than alternative methods of electrical coupling. Including the second internal spring 708 in the main body of the pneumatic coupler 700 electrical network may reduce the need to maintain an alignment and spacing between the poppet spring 704 and the second internal spring 708.

Before moving on, the pneumatic coupler 700 shown in FIG. 7A, may include other components such as, but not limited to a electrical wire contact 714 on the main body of the pneumatic coupler 700, a plastic over mold or press fit potted assembly 716, and a seal volume 718.

In another example, in order to facilitate an improved precision spring length on the internal spring 708 due to limited travel of the poppet 702, a spring contact component may be utilized alternative to a free spring. In a spring contact, the poppet spring 704 may be supported by a piston style housing 720. In addition to the spring contact, in FIG. 7B, the poppet spring 704 may be supported by a piston style housing 720. The example shown in FIG. 7B, may be an alternative method to attach the air exit barb 710 to an isolation bushing 722. Additionally, the example shown in FIG. 7B may illustrate a shorter poppet spring seat 724 in place of the brass/metal insert 706.

Figure 7B:
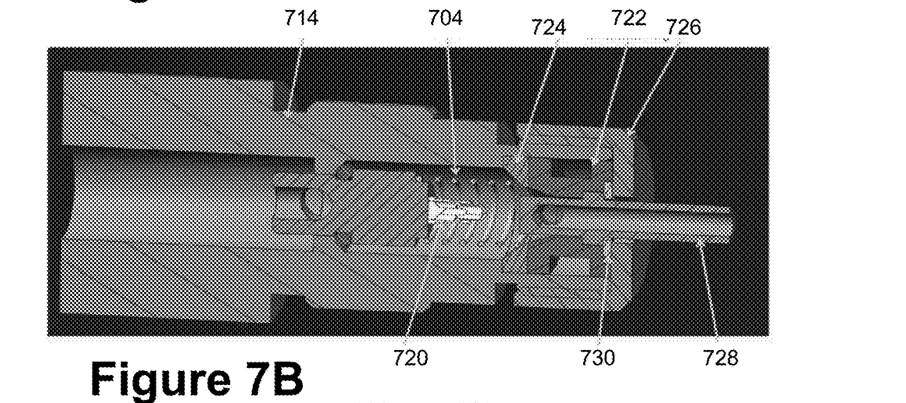

Before moving on, the pneumatic coupler 700 shown in FIG. 7B, may include other components such as, but not limited to a $7/16$ inch thread cap 726, a isolation washer 730 (e.g., may be included if the cap comprise of a conductive material and/or is conductive), and an electrical wire contact on an exit nipple 728.

Figure 7C:
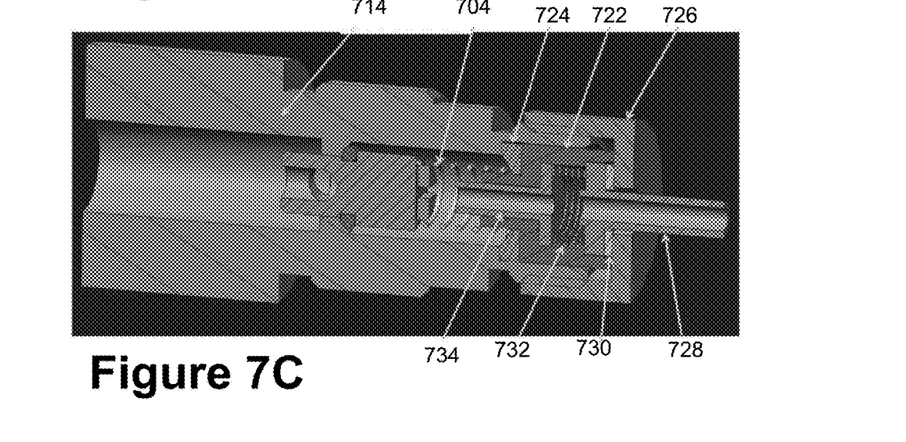

In another example, the need for a custom spring may be reduced by building a compliant element into the isolation bushing 722/barb components 710 as shown in the example of FIG. 7C. In the example shown in FIG. 7C, the air exit barb 710, a switch spring 732, and a switch slider 734 may form an electrical network. The main body of the pneumatic coupler 700, the poppet spring 704, and the poppet seat 724 may form a second electrical network. In this example, when the poppet 702 may be displaced, the poppet 702 may make contact with the switch slider 734 and may complete an electrical circuit between the two electrical networks. It should be mentioned that the term electrical networks may be referred to actual electrical networks and/or conductive networks.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon, that, when executed by a computing device, such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A pneumatic coupler comprising:
   a pneumatic control device;
   a coupler detection module coupled to the pneumatic control device; and
   a signal bearing medium communicatively coupled to the coupler detection module, the signal bearing medium configured to be communicatively coupled to a pneumatic device, the pneumatic device being pneumatically coupled to the pneumatic coupler, and the signal bearing medium being a memory containing one or more of at least an identification of the pneumatic coupler or instructions for a pneumatic device.

2. The pneumatic coupler of claim 1, wherein the pneumatic control device comprises a pneumatic valve device.

3. The pneumatic coupler of claim 2, wherein the pneumatic valve comprises a poppet device.

4. The pneumatic coupler of claim 1, wherein the coupler detection module comprises a device configured to generate an electrical signal.

5. The pneumatic coupler of claim 4, wherein the device configured to generate the electrical signal comprises a transducer device.

6. The pneumatic coupler of claim 4, wherein the device configured to generate the electrical signal comprises an optical proximity detection device.

7. The pneumatic coupler of claim 4, wherein the device configured to generate the electrical signal comprises a switch configured to be activated when the pneumatic coupler is coupled to an intelligent health monitoring device.

8. The pneumatic coupler of claim 1, wherein the coupler detection module comprises:
   a processor;
   a storage medium communicatively coupled to the processor; and
   a radio device communicatively coupled to the processor.

9. The pneumatic coupler of claim 1, wherein the coupler detection module further comprises:
   a power supply.

10. The pneumatic coupler of claim 1, the coupler detection module comprises a radio frequency identification (RFID) tag.

11. The pneumatic coupler of claim 10, wherein the RFID tag comprises a passive RFID tag.

12. The pneumatic coupler of claim 10, wherein the RFID tag comprises a semi-active RFID tag.

13. The pneumatic coupler of claim 10, wherein the RFID tag comprises an active RFID tag.

14. The pneumatic coupler of claim 10, wherein the RFID tag comprises a RFID tag configured to use capacitive technology.

15. A method for pneumatic coupling, the method comprising:
   detecting, at a coupler detection module, a pneumatic coupling by a pneumatic control device, the pneumatic control device having an electrical characteristic based at least in part on a position of the pneumatic control device;
   generating an electrical signal upon detection of the pneumatic coupling, the electrical signal having an electrical signal characteristic based at least in part on the electrical characteristic of the pneumatic control device;
   transmitting the generated electrical signal to a pneumatically coupled device; and
   configuring the pneumatically coupled device based at least in part on the generated electrical signal.

16. A machine readable non-transitory medium having stored therein instructions that, when executed by one or more processors, operatively enable a coupler detection module to:
   detect a pneumatic coupling via a pneumatic control device;
   generate an electrical signal upon detection of the pneumatic coupling, the electrical signal including at least an identification of the pneumatic control device; and
   transmit the generated electrical signal to a pneumatically coupled device to cause the pneumatically coupled device to be configured based at least in part on the electrical signal and the identification of the pneumatic control device.

* * * * *